US012810986B2

(12) United States Patent
Austnes

(10) Patent No.: US 12,810,986 B2
(45) Date of Patent: *Nov. 24, 2026

(54) AUTOMATIC SAFETY ADJUSTMENT SYSTEM

(71) Applicant: CareFusion 303, Inc., San Diego, CA (US)

(72) Inventor: Jan Henning Austnes, Oslo (NO)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/462,823

(22) Filed: Sep. 7, 2023

(65) Prior Publication Data

US 2024/0071592 A1 Feb. 29, 2024

Related U.S. Application Data

(63) Continuation of application No. 17/022,976, filed on Sep. 16, 2020, now Pat. No. 11,783,934.

(Continued)

(51) Int. Cl.
*G16H 20/17* (2018.01)

(52) U.S. Cl.
CPC .................................. *G16H 20/17* (2018.01)

(58) Field of Classification Search
None
See application file for complete search history.

(56) References Cited

U.S. PATENT DOCUMENTS 10,226,571 B2 3/2019 Davis et al.
2003/0135087 A1 7/2003 Hickle et al.

(Continued)

FOREIGN PATENT DOCUMENTS

CN 101721227 A * 6/2010
CN 105074765 A 11/2015

(Continued)

OTHER PUBLICATIONS

Lindell, Colleen. (2018). "Medical Device Alarm Systems: A Multi-Hospital Study of Alarm-Related Events, Caregiver Alarm Response, and their Contributing Factors." Order No. 10808582 The University of Wisconsin—Milwaukee, 2018. Ann Arbor: ProQuest. Web. May 26, 2023. (Year: 2018). 181 pages.

(Continued)

*Primary Examiner* — Lena Najarian

(74) *Attorney, Agent, or Firm* — Mintz Levin Cohn Ferris Glovsky and Popeo P.C.

(57) ABSTRACT

A method may include presenting, on a display of an infusion device, a first patient parameter and a second patient parameter. The infusion device may receive a first entry, which may include a first value of the first patient parameter. The infusion device may determine a default value of the second patient parameter based on the entered first value of the first patient parameter. The infusion device may present the determined default value of the second patient parameter. The infusion device may receive a second entry, which includes a second value of the second patient parameter. The second value may be an adjustment of the default value of the second patient parameter that is an accurate representation of the second patient parameter. Related methods and articles of manufacture, including apparatuses and computer program products, are also disclosed.

16 Claims, 8 Drawing Sheets

Related U.S. Application Data

(60) Provisional application No. 62/901,311, filed on Sep. 17, 2019.

(56) References Cited

U.S. PATENT DOCUMENTS

| | | | | |
|---|---|---|---|---|
| 2008/0177149 | A1 | 7/2008 | Weinert et al. | |
| 2009/0137956 | A1* | 5/2009 | Souter | A61M 5/14244 604/246 |
| 2010/0057488 | A1 | 3/2010 | Broselow | |
| 2012/0277546 | A1* | 11/2012 | Soykan | A61M 1/1601 600/301 |
| 2013/0204433 | A1 | 8/2013 | Gupta et al. | |
| 2014/0180711 | A1* | 6/2014 | Kamen | G16H 40/63 705/2 |
| 2015/0142457 | A1 | 5/2015 | Marshall | |
| 2016/0175076 | A1 | 6/2016 | Hultgren et al. | |
| 2018/0018864 | A1* | 1/2018 | Baker | G08B 21/182 |
| 2019/0189252 | A1 | 6/2019 | Milbrandt et al. | |

FOREIGN PATENT DOCUMENTS

| | | | |
|---|---|---|---|
| CN | 109069736 | A | 12/2018 |
| WO | WO-2013/033025 | A1 | 3/2013 |
| WO | WO-2020/165449 | A1 | 8/2020 |

OTHER PUBLICATIONS

Zhang, W. et al. (2007). “Evaluation of pharmacokinetic parameters of remifentanil Minto in target-controlled infusion in elderly patients.” Clinical Medical Journal of China, vol. 14, No. 02, 3 pages. [English language abstract, p. 1].

* cited by examiner

AUTOMATIC SAFETY ADJUSTMENT SYSTEM

CROSS-REFERENCE TO RELATED APPLICATIONS

This application is a continuation of U.S. patent application Ser. No. 17/022,976, filed Sep. 16, 2020, and titled "Automatic Safety Adjustment System," which claims priority to U.S. Provisional Application No. 62/901,311, filed Sep. 17, 2019, and titled "Automatic Safety Adjustment System," the disclosures of which are incorporated by reference herein in their entireties.

TECHNICAL FIELD

The subject matter described herein relates generally to the dispensation of medications and more specifically to an automatic safety adjustment system for an infusion device for the delivery of anesthesia.

BACKGROUND

Target controlled infusion (TCI) pump systems having an infusion device administer therapy to patients by delivering a medication or other drug to the patient. Pharmacokinetic and pharmacodynamics (Pk/Pd) predictive models may be used in TCI pump systems to calculate drug infusion rates that are used to achieve and maintain a desired target dose of the anesthesia that is delivered to the patient. During initialization of the infusion device and the selected Pk/Pd predictive model, the infusion device requests for the user to enter certain patient parameters, such as the patient's age, height, weight, gender, and the like. Due at least in part to default values of the patient parameters being associated with only one type of patient, regardless of the selected Pk/Pd predictive model, a great burden is placed on the user of the infusion device to enter the correct values of each of the patient parameters, as incorrectly entered values may lead to preparing and/or delivering the incorrect drug dose to the patient or administering a drug dose that causes unintended consequences as a result (e.g., an adverse drug event (ADE), a poor clinical response or outcome, etc.).

SUMMARY

Systems, methods, and articles of manufacture, including computer program products, are provided for initializing a TCI pump system for dispensing a medication to a patient. For example, the system may provide more accurate default values of one or more patient parameters displayed on an infusion device of the TCI pump system to reduce the likelihood that the user of the pump will enter an incorrect value of the patient parameters.

According to some aspects, a method includes presenting, on a display of an infusion device configured to deliver a medication to a patient, a first patient parameter and a second patient parameter of one or more patient parameters. The method may also include receiving, via a user interface of the display, a first entry. The first entry may include a first value of the first patient parameter. The method may further include determining a default value of the second patient parameter based on the entered first value of the first patient parameter. The method may also include presenting, on the display of the infusion device, the determined default value of the second patient parameter. The method may further include receiving, via the user interface, a second entry. The second entry may include a second value of the second patient parameter. The second value may be an adjustment of the default value of the second patient parameter that is an accurate representation of the second patient parameter.

In some aspects, the method also includes determining, based on the first value and the second value, a dose of the medication to be delivered to the patient; and delivering the medication to the patient.

In some aspects, the first patient parameter is an age of the patient, and the second patient parameter is a height of the patient.

In some aspects, the default value of the height of the patient, which is determined based on the entered first value of the age of the patient, is closer to the entered second value of the height of the patient than a predetermined default value of the height of the patient that is not based on the entered first value of the age of the patient.

In some aspects, the determining the default value of the second patient parameter further includes retrieving the default value of the second patient parameter from a data table stored on a data storage in communication with the display. The data table may include one or more default values corresponding to each patient parameter of the one or more patient parameters.

In some aspects, the method further includes: presenting, on the display, a first default value of the first patient parameter before receiving, via the u ser interface, the first entry. The first value of the first patient parameter is lower than the first default value of the first patient parameter. The default value of the second patient parameter is lower than a second default value of the second patient parameter corresponding to the first default value of the first patient parameter.

In some aspects, the method further includes presenting, on the display of the infusion device, a third patient parameter of the one or more patient parameters. The method may also include determining a third default value of the third patient parameter based on one or more of the entered first value of the first patient parameter and the entered second value of the second patient parameter. The method may further include presenting, on the display of the infusion device, the determined third default value of the third patient parameter.

In some aspects, the method also includes receiving, via the user interface, a third entry. The third entry may include a third value of the third patient parameter. The third value may be an adjustment of the third default value of the third parameter that is an accurate representation of the third patient parameter.

In some aspects, the first patient parameter is an age of the patient, the second patient parameter is a height of the patient, and the third patient parameter is a weight of the patient.

Implementations of the current subject matter can include methods consistent with the descriptions provided herein as well as articles that comprise a tangibly embodied machine-readable medium operable to cause one or more machines (e.g., computers, etc.) to result in operations implementing, or signaling the need to implement, one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to initializing a TCI pump system, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
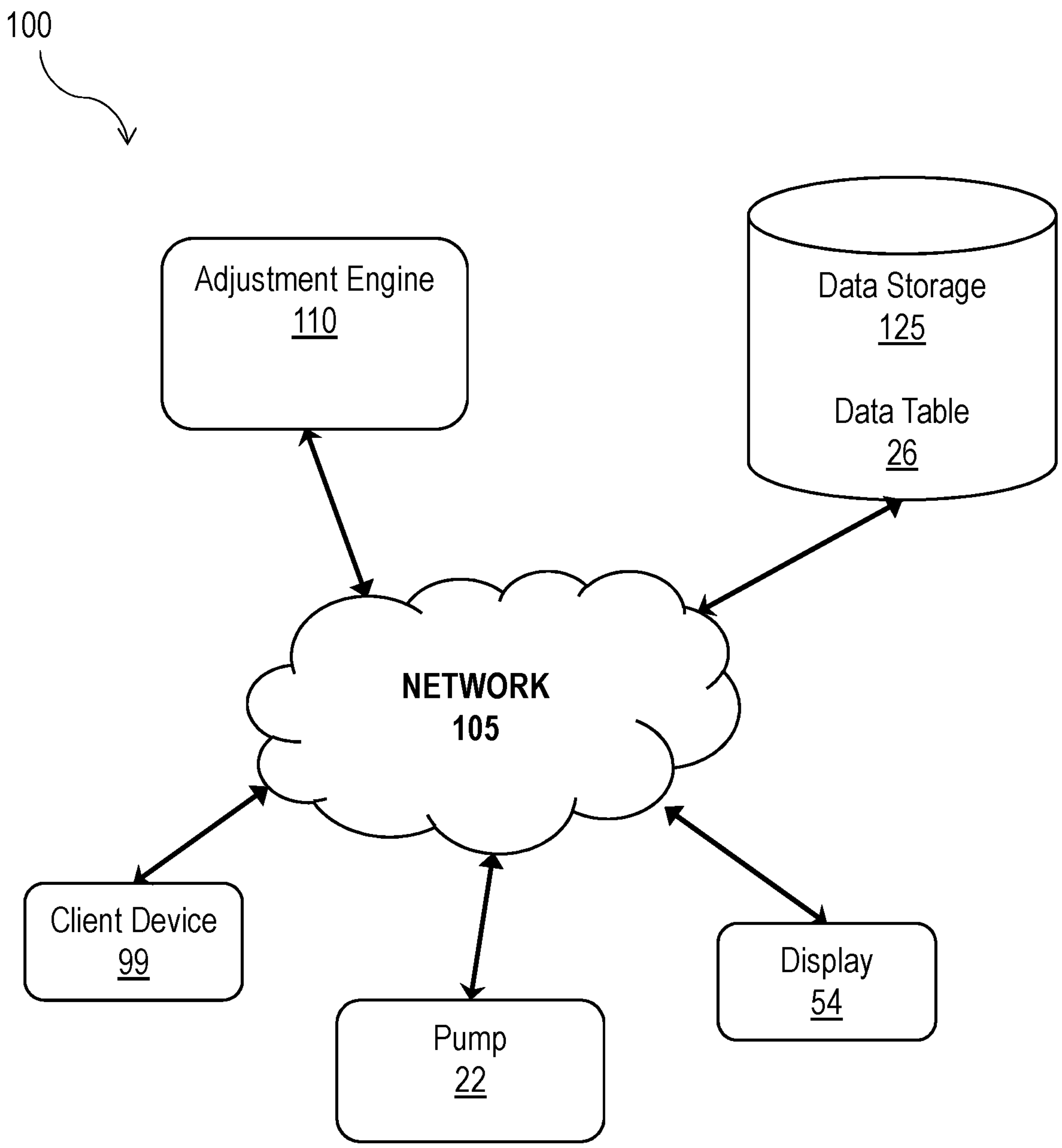
FIG. 1 depicts a system diagram illustrating an automatic safety adjustment system, in accordance with some example embodiments.

Target controlled infusion (TCI) pump systems having an infusion device administer therapy to patients by delivering a medication or other drug (e.g., anesthesia, such as propofol, remifentanil, and the like) to the patient. Pharmacokinetic and pharmacodynamics (Pk/Pd) predictive models (e.g., Eleveld propofol and/or remifentanil TCI models and/or another predictive model such as a Bayesian-based model) may be used in TCI pump systems to calculate drug infusion rates that are used to achieve and maintain a desired target dose of the drug that is prepared and/or delivered to the patient. The Pk/Pd models may be loaded onto and stored on the infusion device, and are available at initialization of the infusion device for the user (e.g., a clinician, the patient, etc.) to select the desired Pk/Pd model. During initialization of the infusion device and the selected Pk/Pd predictive model, the infusion device requests for the user to confirm, select, and/or otherwise enter one or more patient parameters of the patient, such as the patient's age, height, gender, weight, and the like. Using these patient parameters, the TCI pump system may individualize the drug doses that are delivered to each patient, and may calculate optimal infusion profiles for each patient. Thus, the value of each of the patient parameters entered by the user directly impacts a dose of the drug that is delivered to the patient, and an incorrectly entered value may lead to an over- or under-medicated patient.

Before each value of the patient's parameters (e.g., age, height, gender, weight, etc.) is entered into the infusion device, the infusion device displays a default value of the patient parameter. Infusion devices that use certain Pk/Pd models, such as Eleveld models, for example, are unique in that they allow the user to program the infusion devices to be able to handle a wide range of a patient population, ranging from children to adults of various heights, weights, genders, and the like. Even so, when the infusion devices are initialized, the default values of the patient parameters displayed by the infusion device to the user are typically associated with only one type of patient, such as an adult patient. This is particularly problematic if the patient is a child or otherwise has one or more patient parameters that are significantly different than the displayed default value, as it places a great burden on the user to enter the correct value into the infusion device. The automatic safety adjustment system described herein helps to reduce the burden on the user to enter the correct value of one or more of the patient parameters, by, for example, automatically adjusting a default value of the patient parameters based on one or more previously entered values of the patient parameters. This helps to prevent or reduce the likelihood that the user will enter the incorrect value (e.g., the incorrect height or weight of the patient), thereby preventing or reducing the likelihood of improperly operating the infusion device so that it under- or over-doses the patient, or otherwise delivers the incorrect dose of the drug to the patient. Thus, this helps to minimize the risk of an ADE, such as toxicity, end organ damage, and/or other measurable poor outcomes caused by under-dosing or over-dosing. This may also help to better predict the offset of the medications provided to the patient and may allow for better patient-room planning at a medical facility.

As an example, regardless of the age entered into the infusion device by the user, the default age of the patient may be set to 50 years old and, the default values of the remaining patient parameters may be based on the default setting of the patient being 50 years old (e.g., the default height is set to 170 cm and the default weight is set to 70 kg). This places a significant burden on users of the infusion device when the patient is not an average adult, such as when the patient is a child or an elderly person, or when the patient is significantly shorter, taller, heavier, or lighter than the default adult, to select the correct height, weight, gender, etc. of the patient, thereby increasing the likelihood that a user error will occur. As noted above, incorrectly entered values of the one or more of the patient parameters, such as the user's age, height, gender, weight, and the like, can lead to significant medical issues, as the infusion device will deliver a dose of the drug to the patient that is too high or too low.

Additionally, a user of the infusion device may accidentally confirm a default or incorrect value of one or more of the patient parameters that is displayed on the infusion device. In such instances, since the infusion device would still display a default value of the subsequent patient parameter associated with an average adult (for example), the user of the infusion device may be unaware of the error in the entry of the value of the patient parameter. This situation is likely to occur in emergency situations, when the user is distracted, rushed, and/or is otherwise not focused on entering the correct values of the patient parameters, and when it is even more important for the correct values of each of the patient parameters to be entered.

In other examples, a user may be asked to sequentially enter and/or confirm at least the patient's age, height, gender, and weight. In these examples, after the user enters and/or confirms the patient's age, the infusion device displays the default height to the user (which as noted above, is a default height of an average adult). In some embodiments, the user may then enter the patient's gender. After that, the user may enter (select, scroll to, etc.) the actual value of the patient's height. Regardless of the patient's age, the patient's height, and/or the patient's gender, the infusion device will then still display the default weight to the user (which, like the default height, is a default weight of an average adult). In both cases, this places a significant burden on users to, for example, enter and/or confirm the correct height and weight of the patient. User errors made in the entry of the value of each of the patient parameters may be compounded when errors are made in more than one patient parameter, such as when an error is made in the entered patient height, and another error is made in the entered patient weight, thereby furthering the damage to the patient caused by the user error.

An automatic safety adjustment system for an infusion device, consistent with implementations of the current subject matter may address one or more of these issues, by, for example, automatically adjusting and displaying a more accurate default value of one or more of the patient parameters (e.g., height, weight, and the like) on the infusion device, based on the value of one or more of the previously entered patient parameters (e.g., age, height, gender, weight, and the like). In some example embodiments, the infusion device may, after receiving a user entry of the value of one or more of the patient parameters, automatically adjust the value of one or more of the patient parameters to a more accurate default value that is closer to the actual value of the one or more patient parameters of the patient.

FIG. 1 depicts a system diagram illustrating an automatic safety adjustment system 100, in accordance with some example embodiments. Referring to FIG. 1, the automatic safety adjustment system 100 may include an adjustment engine 110, a pump (also referred to herein as an "infusion device") 22, a display 54, and a data storage 125. In some example embodiments, the adjustment engine 110, the display 54, and/or the data storage 125 may form a portion of the pump 22 and/or may be positioned within a housing of the pump 22.

The display 54 may form a part of the pump 22 or may be separately coupled as part of a client device 99. The display 54 may also include a user interface. The user interface may form a part of a display screen of the display 54 that presents information to the user and/or the user interface may be separate from the display screen. For example, the user interface may be one or more buttons, or portions of the display screen that is configured to receive an entry from the user.

The client device 99 may be a mobile device such as, for example, a smartphone, a tablet computer, a wearable apparatus, and/or the like. However, it should be appreciated that the client device 99 may be any processor-based device including, for example, a desktop computer, a laptop or mobile computer, a workstation, and/or the like. For example, via the client device 99, the user may be able to configure certain parameters of the pump 22, such as an air in line threshold, a rate limit, an alarm limit, and the like. Additionally, in some examples, via the client device 99, the user may configure various drug protocols with default settings and safety parameters (e.g., setting a limit to a dose of a drug).

The data storage 125 may include databases and/or data tables, such as a data table 26, providing physical data storage within a dedicated facility and/or being locally stored on the pump 22. Additionally and/or alternatively, the data storage 125 may include cloud-based systems providing remote storage of data in, for example, a multi-tenant computing environment and/or the like. The data storage 125 may also include non-transitory computer readable media.

As FIG. 1 shows, the adjustment engine 110, the pump 22, the display 54 and/or the data storage 125 may be communicatively coupled via a network 150. Meanwhile, the network 150 may be any wired and/or wireless network including, for example, a public land mobile network (PLMN), a local area network (LAN), a virtual local area network (VLAN), a wide area network (WAN), the Internet, and/or the like.

The pump 22 may be a TCI pump (e.g., a TCI pump having one or more Pk/Pd models), a syringe pump, an anesthesia delivery pump, and/or a patient-controlled analgesic (PCA) pump configured to deliver a medication (e.g., an anesthesia, such as propofol and/or remifentanil, and the like) to a patient. However, it should be appreciated that the pump 22 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like. Alternatively, the pump 22 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like. Moreover, the pump 22 may be part of a patient care system that includes one or more additional pumps.

The pump 22 may be configured to receive one or more syringes containing a medication (e.g., an anesthesia) such as, for example, propofol and/or remifentanil, and the like. The syringe may be inserted into the pump 22 such that the pump 22 may deliver the medication to the patient in one or more doses, having one or more drug doses.

The pump 22 (or infusion device) may determine the optimal dose of the medication to deliver to the patient based on the values of one or more patient parameters, including the patient's age, height, weight, gender, laboratory results, whether the patient has ingested opiates, the patient's BMI, and the like. In some embodiments, the pump 22 may display the one or more patient parameters on the display 54. Before determining the optimal dose of the medication and/or delivering the medication to the patient, such as during initialization of the pump 22, the pump 22 may display, via the display 54, a request to the user for the user to enter and/or confirm a value of each of the one or more patient parameters.

Figure 2:
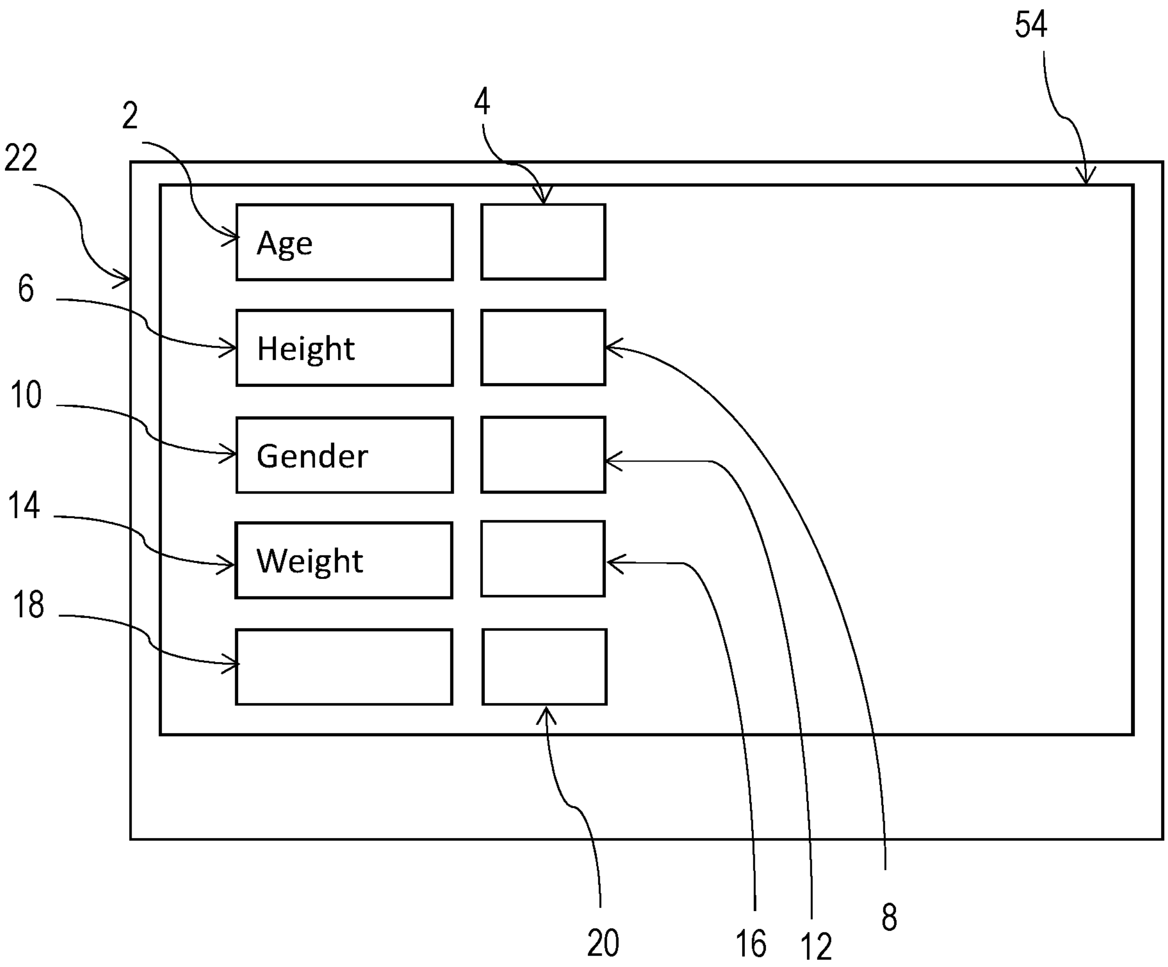
FIG. 2 schematically depicts an example pump having a display, in accordance with some example embodiments.

FIG. 2 schematically illustrates an example of the display 54 of the pump 22. As shown in FIG. 2, the one or more patient parameters displayed on the display 54 includes a first patient parameter 2, a second patient parameter 6, a third patient parameter 10, and a fourth patient parameter 14. In some embodiments, the one or more patient parameters also includes a fifth patient parameter 18 and/or more patient parameters. The first patient parameter 2 may correspond to the patient's age, the second patient parameter 6 may refer to the patient's height, the third patient parameter 10 may refer to the patient's gender, the fourth patient parameter 14 may refer to the patient's weight, and the fifth patient parameter 18 may refer to the patient's body mass index (BMI) and/or the patient's opiate use, for example. The patient parameters may also be arranged in other orders.

The first patient parameter 2 includes a corresponding first patient parameter value 4, the second patient parameter 6 includes a corresponding second patient parameter value 8, the third patient parameter 10 includes a corresponding third patient parameter value 12, the fourth patient parameter 14 includes a corresponding fourth patient parameter value 16, and the fifth patient parameter 18 includes a corresponding fifth patient parameter value 20. The first, second, third, fourth, and fifth patient parameter values 4, 8, 12, 16, 20 may be entered by the user on the display 54 and/or calculated by the infusion device and the display 54 may receive the user's entry. In some embodiments, the display 54 does not initially display a value for each of the first, second, third, fourth, and fifth patient parameter values 4, 8, 12, 16, 20 and the user enters the value for one or more of the first, second, third, fourth, and fifth patient parameter values 4, 8, 12, 16, 20. In other embodiments, the display 54 first displays a default value for each of the first, second, third, fourth, and fifth patient parameter values 4, 8, 12, 16, 20, and the display 54 may receive the user's confirmation of the displayed default value for the first, second, third, fourth, and fifth patient parameter values 4, 8, 12, 16, 20, and/or the display 54 may receive the user's entry or selection of the value for each of the first, second, third, fourth, and fifth patient parameter values 4, 8, 12, 16, 20.

For example, the user may confirm the default value displayed by the display 54, enter a new value in place of the displayed default value, scroll to a new value beginning at the default value, and the like. The value of the corresponding patient parameter may be considered entered as described herein, when the display 54 receives the user's selection of the value using methods, such as those described herein. The display 54 may simultaneously display the default values for each of the first, second, third, fourth, and fifth patient parameter values 4, 8, 12, 16, 20 and/or sequentially display the default values for each of the first, second, third, fourth, and fifth patient parameter values 4, 8, 12, 16, 20 (e.g., the default value for the second patient parameter value 8 is displayed via the display 54 after entry of the first patient parameter value 4 is received by the display 54, the default value for the third patient parameter value 12 is displayed via the display 54 after entry of the second patient parameter value 8 is received by the display 54, and so on).

Figure 3A:
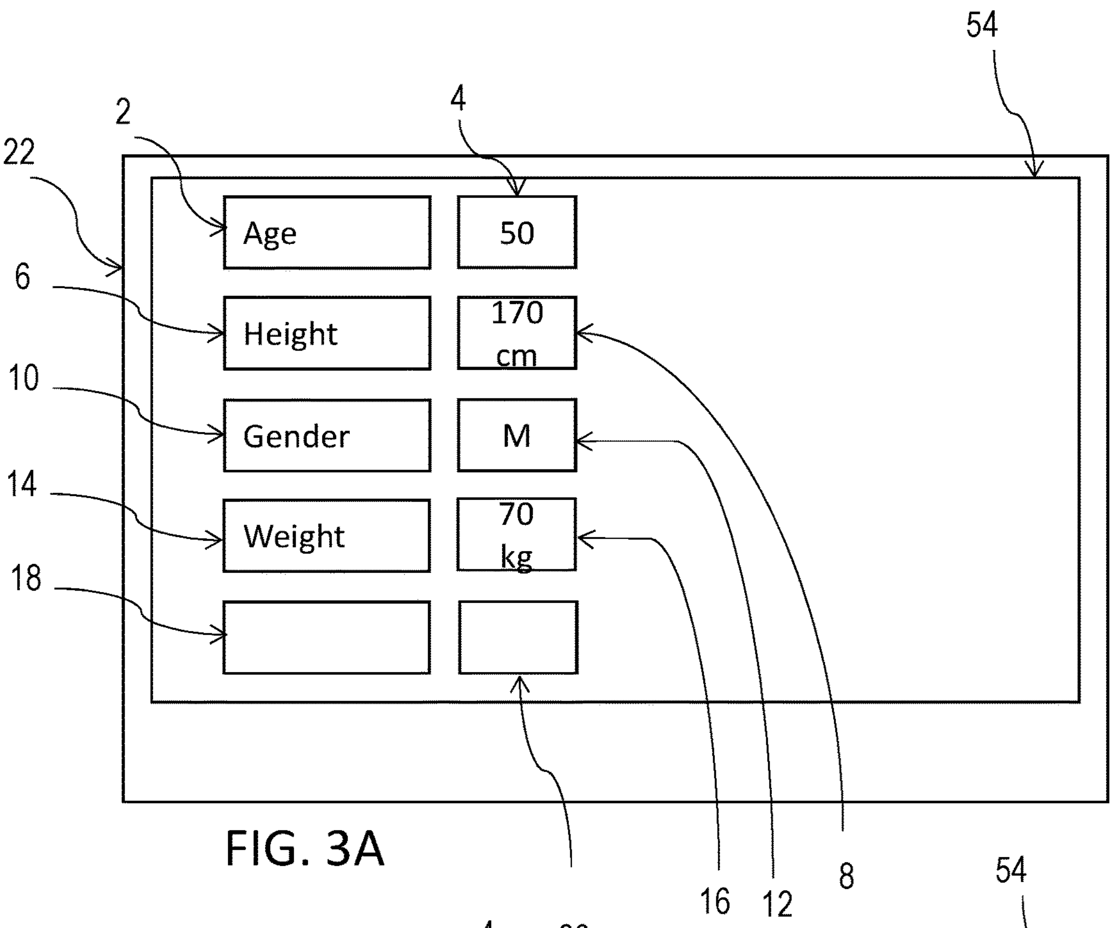
FIG. 3A schematically depicts another example pump having a display, in accordance with some example embodiments.
Figure 3B:
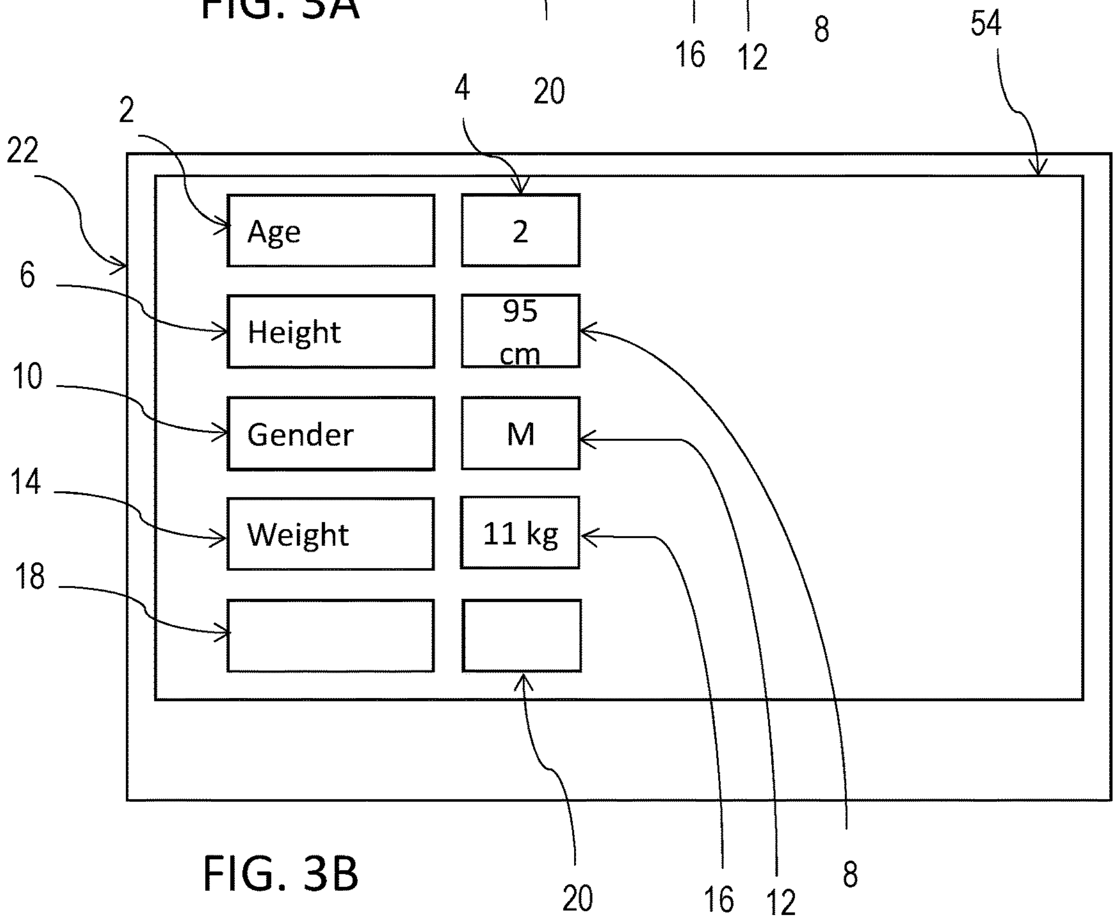
FIG. 3B schematically depicts another example pump having a display, in accordance with some example embodiments.

FIGS. 3A and 3B schematically illustrate examples of the display 54, such as upon initialization of the pump 22, or after selection of a predictive model, such as a Pk/Pd model (e.g., Eleveld propofol and/or remifentanil TCI models and/or a predictive model such as a Bayesian-based model) is received by the pump 22. The predictive model can be singular or multiple in nature.

In some embodiments, the display 54 initially displays a default value corresponding to each of the patient parameters for a patient based on a predetermined default value of the first patient parameter (e.g., the patient's age). In some embodiments, the display 54 displays the default value of each of the patient parameters for the patient after entry of the first patient parameter value 4 is received by the display 54. In other embodiments, the display 54 displays the default value of the second patient parameter value 8 after receipt of the entry of the first patient parameter value 4, based on the entered first patient parameter value 4, displays the default value of the third patient parameter value 12 based on the entered first and/or second patient parameter values 4, 8, and so on.

In the example shown in FIG. 3A, the default value and/or the entered value of the first patient parameter 2 is 50 years old, and in the example shown in FIG. 3A, the default value and/or the entered value of the first patient parameter 2 is 2 years old. Once the pump 22 receives the user's entry of the value of the patient's age, the pump 22 (e.g., the adjustment engine 110) may determine and display, via the display 54, a default value of the patient's height (e.g., the second patient parameter 6) that corresponds to the entered age (e.g., the first patient parameter 2) of the patient, rather than a predetermined default value that is displayed regardless of the patient's age entered by the user. The user of the pump 22 may then be able to confirm and/or alter the adjusted default value of the patient's height (e.g., the second patient parameter 6) to the actual value of the patient's height. Based on the actual value of the patient's age, height, and/or gender, for example, the pump 22 may determine and display to the user (such as by the adjustment engine 110), via the display 54, a default value of the patient's weight.

In this example, if the value of the patient's age received by the display of the pump 22 is 2 years old (e.g., as shown in FIG. 3B), the adjustment engine 110 of the pump 22 may communicate with the data storage 25 to retrieve, from a data table 26 stored on the data storage 25, and display, at the display 54, a default value of the patient's height that corresponds to the entered value of the patient's age. Table 1 below illustrates an example of the data table 26 stored on the data storage 25:

TABLE 1

| Age (years old) | Height (cm) | Weight (kg) |
|---|---|---|
| 0 to 1 | 68 | 8 |
| 1 to 2 | 85 | 11 |
| 2 to 5 | 95 | 15 |
| 5 to 10 | 115 | 25 |
| 10 to 15 | 155 | 45 |
| 15 to 20 | 170 | 60 |
| >20 | 170 | 70 |

In some embodiments, the adjustment engine 110 of the pump 22 automatically adjusts the default value of the patient's height from a predetermined default height (which may be based on an adult patient), to a different (e.g., lower or higher) value associated with the patient's age. For example, rather than displaying a default value of the patient's height, the pump 22 may automatically adjust the default value of the patient's height from 170 cm, which is the value of the height associated with an adult patient. The pump 22 may automatically adjust the default value to a default value of the patient's height that is closer to the patient's actual height (which in the example of a 2 year old patient would be 85 cm). In this example, the display 54 may then display the default value of the patient's height of 85 cm, for the user to enter the actual value of the patient's height. This reduces the risk of erroneous input by the user of the values of the one or more patient parameters, at least because the user of the pump 22 would be more likely be alerted to an incorrectly entered patient parameter (e.g., the user previously entered in the incorrect age of the patient). If the determined default values of the subsequently displayed patient parameters do not align with the user's expectations for the values of those patient parameters, the user of the pump 22 would also be less likely to select the incorrect height or weight of the patient, since the displayed default value would be closer to the actual value of the patient parameter, such as the height and/or weight of the patient. Additionally, this helps to ensure that the correct drug dose is delivered to the patient, as the entered values of each of the one or more patient parameters would more accurately reflect the characteristics of the target patient.

The display (e.g., a dynamic display) also improves the manner in which the pump 22 displays information and interacts with the user. By dynamically generating values based on an initial input, the pump 22 may reduce the need to render additional complex data entry elements to complete programing. For example, the graphical user interface presented by the display may include graphical elements to increment or decrement a value rather than presenting a full keypad for data entry. The pump 22 may more efficiently process and validate these input signals, which may be more than entries from freeform text or numeric data entry fields. The use of smaller entry elements also conserves display area on the pump display. This permits presentation of more programming parameters at the time of data entry thereby further reducing the likelihood of a programming error.

Figure 4:
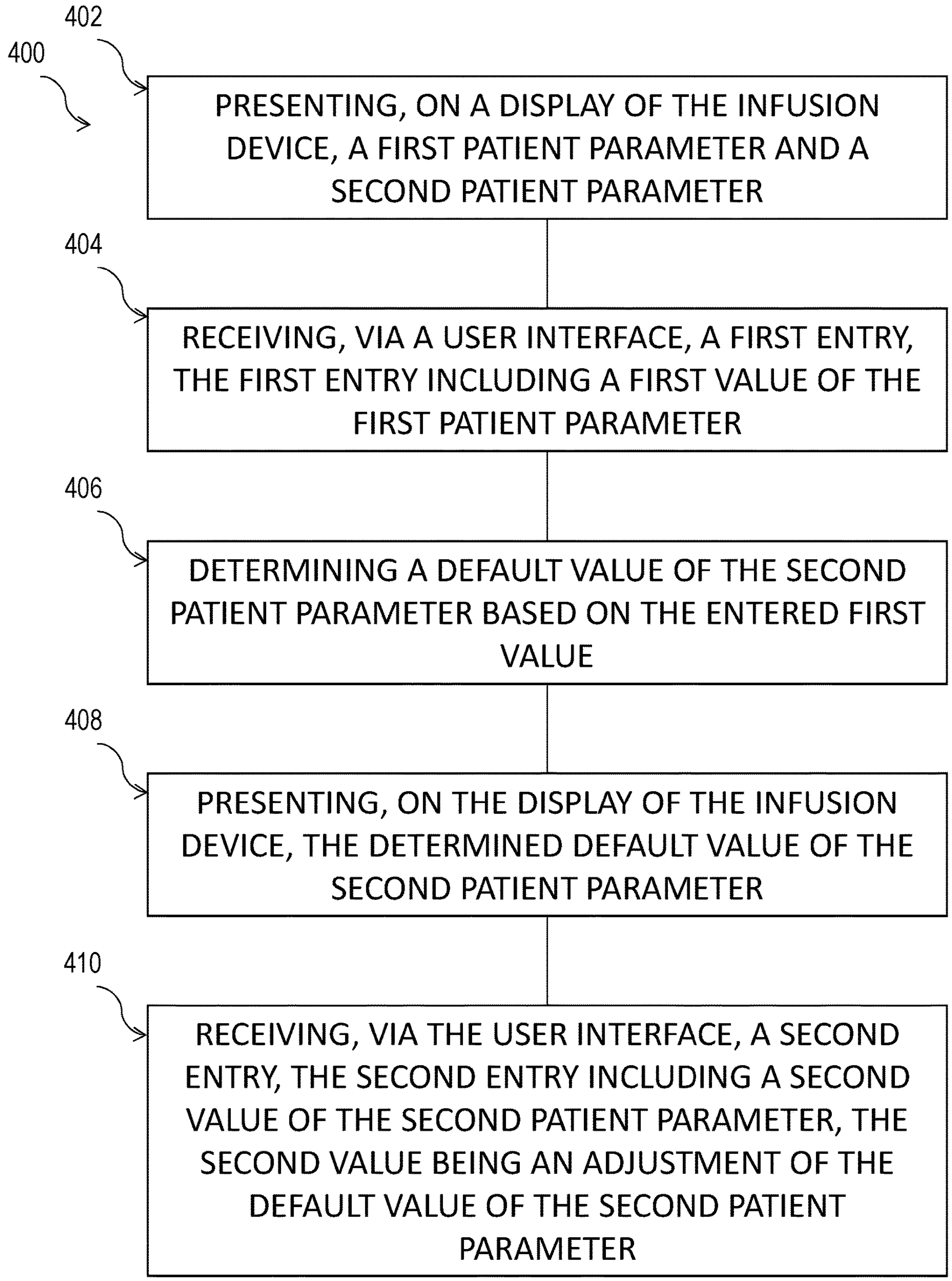
FIG. 4 depicts a flowchart illustrating a process for initializing a TCI pump system, in accordance with some example embodiments.

FIG. 4 depicts a flowchart illustrating a process 400 for adjusting a default value of one or more patient parameters for an infusion device that delivers a medication to a patient, in accordance with some example embodiments. Referring to FIG. 4, the process 400 may be performed by the parameter adjustment system 100, such as by the adjustment engine 110 or another component of the pump 22.

In some embodiments, an infusion device (the pump 22) is initialized and/or the infusion device receives a selection of one or more Pk/Pd models on the infusion device, such as via a user interface of a display of the infusion device. Initialization of the infusion device may include obtaining one or more parameters, establishing one or more connections with data sources for inputs to the process 400, identifying one or more of the predictive models for processing the inputs to the process 400, and/or the like.

The infusion device may additionally and/or alternatively receive one or more pump parameters (e.g., air in line thresholds, rate limits, alarm limits, and the like) and/or drug protocol settings and safety parameters (e.g., a dose limit) that are entered directly on the infusion device, such as via the user interface or received from a client device. The one or more pump parameters and/or drug protocol settings and safety parameters may include static values provided as a configuration to the parameter adjustment system 100. Additionally and/or alternatively, the one or more pump parameters and/or drug protocol settings and safety parameters may be dynamically generated to tailor the one or more pump parameters and/or drug protocol settings and safety parameters to specific characteristics of the medical facility (e.g., number of beds, number of clinicians, average patient stay duration, age of facility, etc.) and/or patient(s) under analysis (e.g., typical condition, medication dispensed, demographics, etc.).

In some implementations, an appropriate model may be identified based on programming parameters for the infusion device such a care area, drug to be infused, or module used to deliver the medication (e.g., syringe module, large volumetric pump, etc.). The models may be associated with one or more the programmed parameters and used to select a model. In some implementations, the set of models known to the infusion device may be narrowed (e.g., filtered) based on one or more values received by the infusion device. In such instances, the user may be presented with a subset of models that could apply from which a selection of models to actually activate may be received.

At 402, one or more patient parameters may be presented on a display, such as the display 54, coupled to or otherwise forming a part of the infusion device. The one or more patient parameters may be presented on the display at initialization of the infusion device, or at a later time. For example, at least a first patient parameter (e.g., a patient's age), such as the first patient parameter 2, and a second patient parameter, such as the second patient parameter 6, (e.g., a patient's height, gender, or weight), may be presented on the display. In some embodiments, one or more additional patient parameters may be presented on the display of the infusion device, such as a third patient parameter, such as the third patient parameter 10 (e.g., a patient's height, gender, or weight), a fourth patient parameter (e.g., a patient's height, gender, or weight), such as the fourth patient parameter 14, and a fifth patient parameter (e.g., a patient's opiate intake and/or a patient's BMI), such as the fifth patient parameter 18, or other patient parameters.

In some embodiments, the display presents a value corresponding to each of the one or more patient parameters. For example, the display may present a value of the first patient parameter after entry of the value of the first patient parameter by the user. In other examples, the display may present a first default value of the first patient parameter before receiving the entry of the value by the user. For example, the display may present a default value for at least the first patient parameter, the second patient parameter, the third patient parameter, the fourth patient parameter, and/or the fifth patient parameter. In this example, the infusion device may send a request to the user for confirmation (such as via the user interface) of the default value for at least the first patient parameter, and/or entry of another value (such as via the user interface) for at least the first patient parameter. As explained in more detail below, when the entered value of the first patient parameter is lower than the first default value of the first patient parameter displayed to the user, the default value of the second patient parameter may be lower than a second default value of the second patient parameter corresponding to the first default value of the first patient parameter.

At 404, the infusion device (e.g., via the display) receives a first entry by the user, such as via the user interface. The first entry may be the first value of the first patient parameter. The user may enter the first value by, for example, selecting, confirming, and/or scrolling to the first value. In some embodiments, as noted above, the display may first present a default value of the first patient parameter. The user may adjust the default value by entering the first value of the first patient parameter.

At 406, the infusion device (e.g., via the adjustment engine 110) may determine a default value of a subsequent patient parameter based on one or more entered values of the previously entered patient parameters. For example, the adjustment engine 110 may determine a default value of the second patient parameter based on the entered first value of the first patient parameter. For example, the adjustment engine 110 may retrieve the default value of the second patient parameter from a data table stored on the data storage (such as the data storage 25). The data table (which may include data table 1) may include one or more default values corresponding to each value or range of values entered for each patient parameter of the one or more patient parameters.

In some embodiments, the determined default value of, for example, the second patient parameter is closer to the actual value of the second patient parameter entered by the user and received by the infusion device than a predetermined default value that is not based on the entered first value of the first patient parameter. Depending on the entered value for the first patient parameter received by the infusion device, the default value of the second patient parameter may be higher or lower than the predetermined default value.

For example, as discussed above with respect to FIGS. 3A-3B, if the predetermined default value of the patient's height corresponds to a person of age 50, and the patient is a child of age 2, the determined default value of the height of the patient (e.g., the second patient parameter) may be lower than default height associated with a person of age 50, and may be closer to the actual height of the patient. Thus, the first value of the first patient parameter may be lower than the first default value of the first patient parameter, and the default value of the second patient parameter may be lower than a second default value of the second patient parameter corresponding to the first default value of the first patient parameter. Even in implementations, in which the predetermined default value is not determined or does not exist, determining the second default value of the subsequent patient parameters based on one or more of the previously entered patient parameter (e.g., in this case, the default value of the second patient parameter is based on the entered value of the first patient parameter), may result in the determined second default value being closer to the actual value of the second patient parameter. This may reduce the likelihood of user error, thereby further preventing or reducing the likelihood of delivering an incorrect dose of the medication to the patient.

At 408, the display of the infusion device may present the determined default value of the second patient parameter to the user. In some examples, the adjustment engine 110 transmits the determined default value of the second patient parameter to the u ser. The user may then enter the actual value of the second patient parameter by, for example, selecting, confirming, and/or scrolling to the second value of the second patient parameter.

At 410, the display receives the second entry by the user, such as via the user interface. The second entry includes the second value of the second patient parameter, which may be higher, lower, the same as, or otherwise adjusted from the default value of the second patient parameter that was presented to the user. The second value entered by the user and received by the infusion device is an accurate representation of the second patient parameter. The second value may be relatively close to the second default value. In some embodiments, the second value is closer to the second default value than the predetermined default value of the second patient parameter.

Though this method is described with respect to the first patient parameter and the second patient parameter, the method may also be applied to the third, fourth and/or fifth patient parameters. For example, with respect to the third patient parameter, the display of the infusion device may present the third patient parameter, and so on. The infusion device (e.g., the adjustment engine) may determine a third default value of the third patient parameter based on one or more of the previously entered first value of the first patient parameter and the previously entered second value of the second patient parameter. The infusion device may present, on the display of the infusion device, the determined third default value of the third patient parameter, which may be relatively close to the actual value of the third patient parameter. In some embodiments, the infusion device (via the display) receives a third entry by the user. The third entry may include a third value of the third patient parameter, which is an accurate representation of the third patient parameter. The third value may be adjusted from and/or may be the same as the third default value of the third patient parameter.

Based on the entered values of the one or more patient parameters, such as the first patient parameter, the second patient parameter, the third patient parameter, the fourth patient parameter, and/or the fifth patient parameter, the infusion device may determine a dose of medication to deliver to the patient. The infusion device may then delver the medication to the patient.

In some implementations, a value generated by the model may be used to validate a user entry. For example, the value may represent a target parameter value. If a programmed value for the parameter does not correspond to the target parameter value, the pump may adjust one or more functions. For example, if the programmed value does not fall within a predetermined threshold of the target parameter value, the pump may disable power to a pumping motor or other hardware element of the pump. In some implementations, the adjustment may include adjusting a user interface or elements presented thereon. For example, a programming user interface may include a start element that, when activated, provides a signal to initiate fluid pumping according to the programmed parameters. If the programmed value is out of range of the target parameter value, the start element may be deactivated or hidden from the user.

Figure 5:
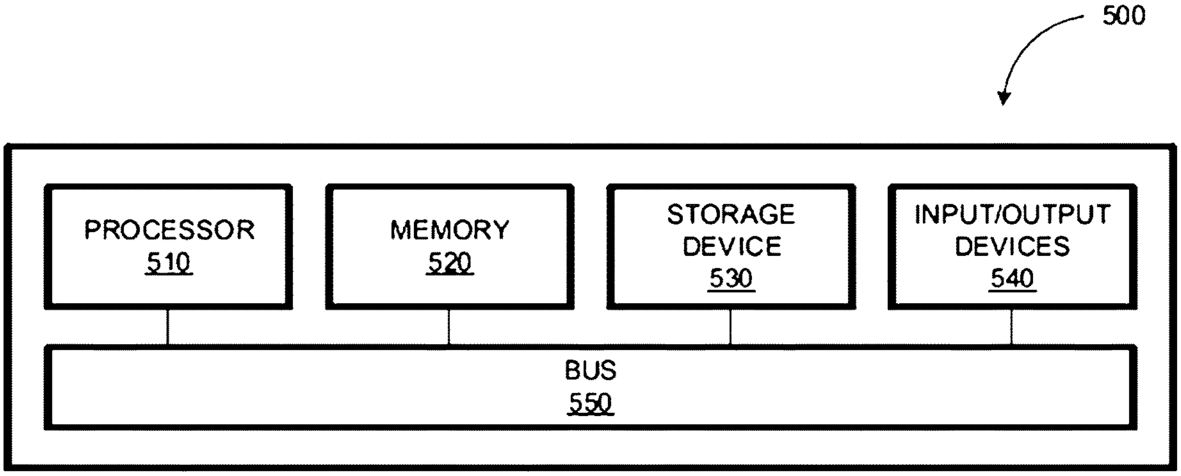
FIG. 5 depicts a block diagram illustrating a computing system, in accordance with some example embodiments.

FIG. 5 depicts a block diagram illustrating a computing system 500 consistent with implementations of the current subject matter. Referring to FIGS. 1 and 5, the computing system 500 can be used to implement the pump 22, the adjustment engine 110 and/or any components therein.

As shown in FIG. 5, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the adjustment engine 110. In some example embodiments, the processor 510 can be a single-threaded processor. Alternatively, the processor 510 can be a multi-threaded processor. The processor 510 is capable of processing instructions stored in the memory 520 and/or on the storage device 530 to present graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some example embodiments, the input/output device 540 includes a keyboard and/or pointing device. In various implementations, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

Figure 6A:
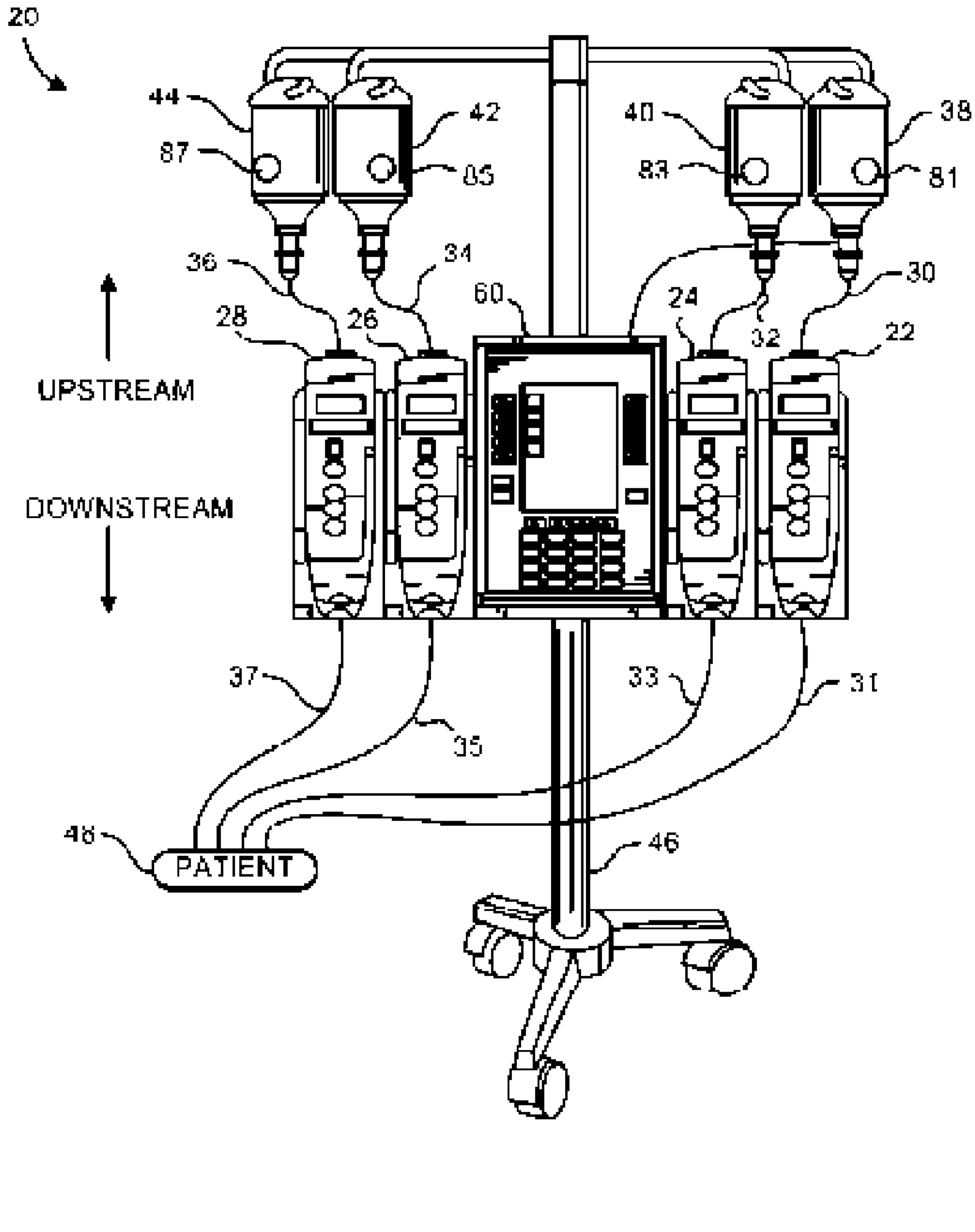
FIG. 6A depicts a front view of a patient care system, in accordance with some example embodiments.
Figure 6B:
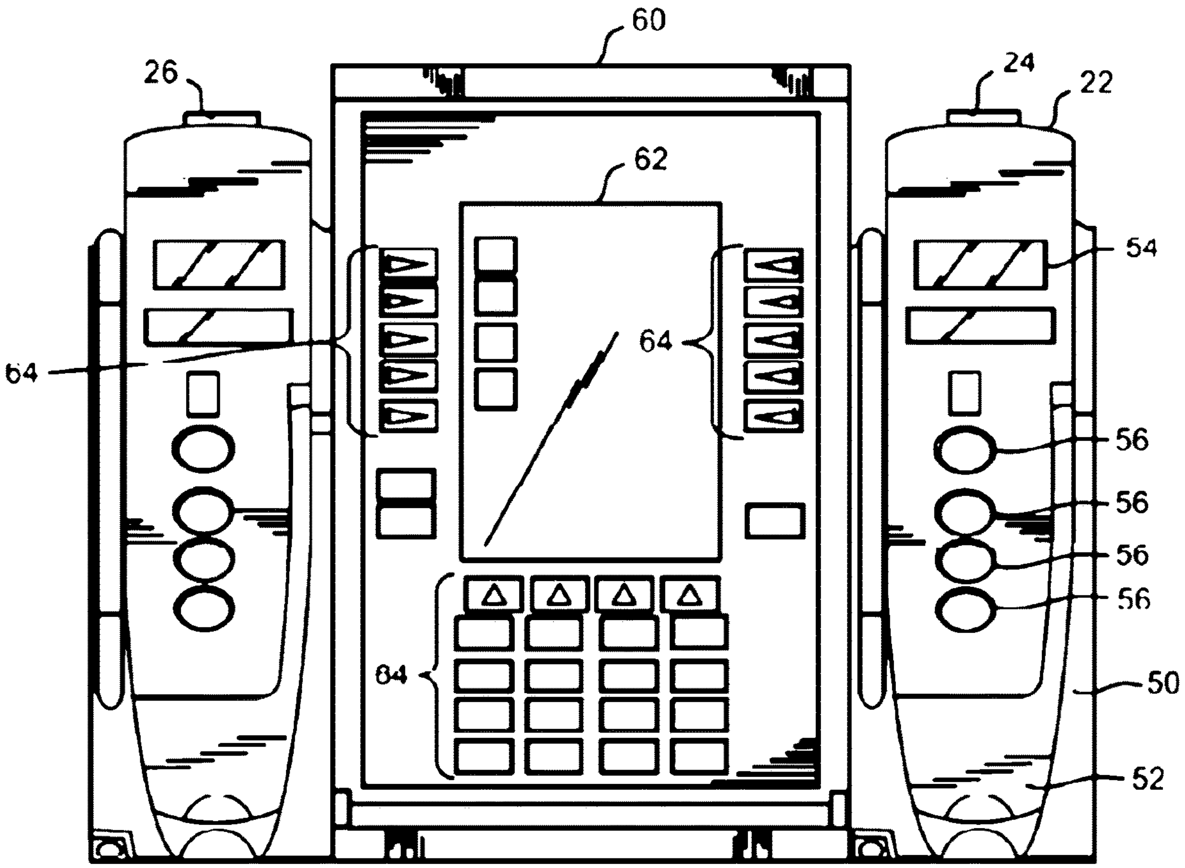
FIG. 6B depicts an enlarged view of a portion of a patient care system, in accordance with some example embodiments.
Figure 6C:
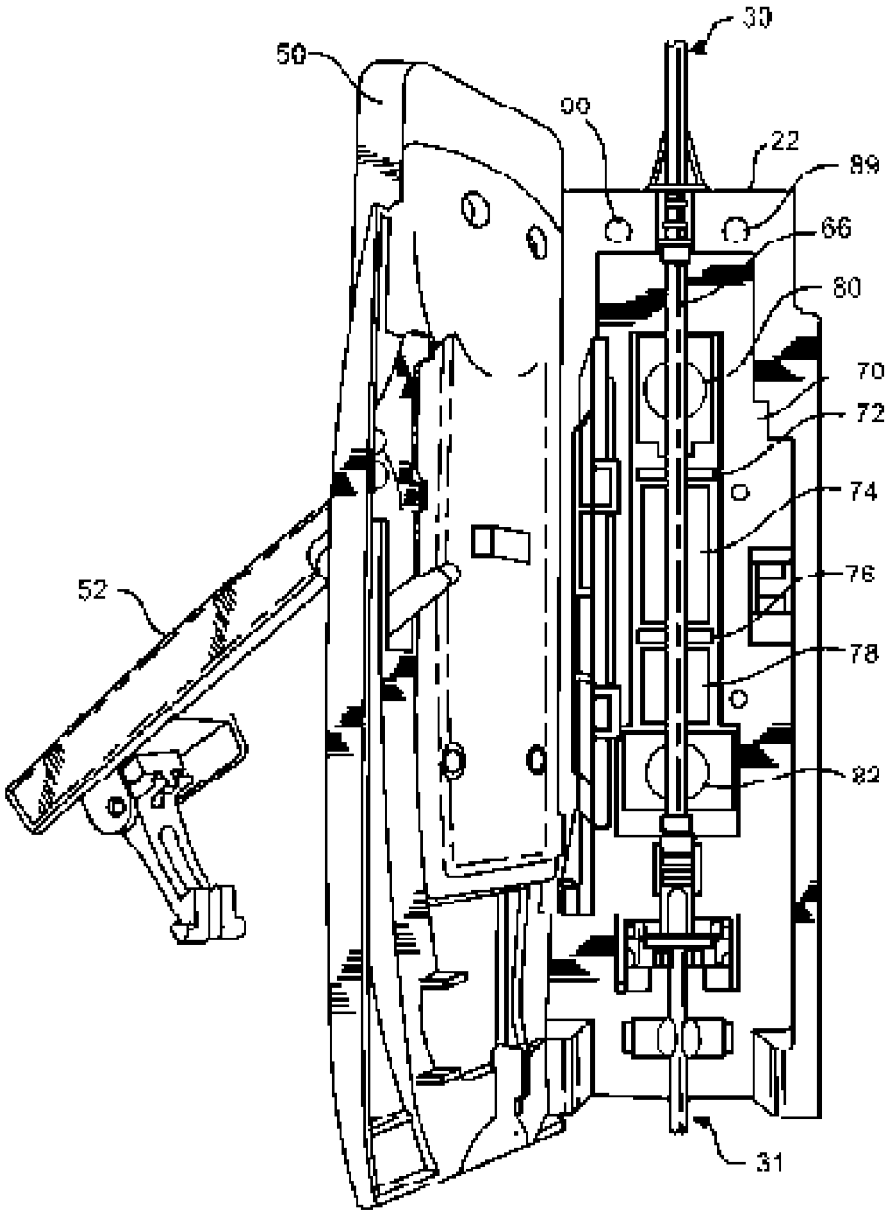
FIG. 6C depicts a perspective view of a pump, in accordance with some example embodiments.

In some example embodiments, the pump 22 may be part of a patient care system 20. FIGS. 6A-6C illustrate example embodiments of the patient care system 20, though other types of patient care systems may be implemented. Referring to FIG. 6A, the patient care system 20 may include the pump 22 as well as additional pumps 24, 26, and 28. Although a large volume pump (LVP) is illustrated, other types of pumps may be implemented, such as a small volume pump (SVP), a TCI pump (e.g., a TCI pump having one or more Pk/Pd models), a syringe pump, an anesthesia delivery pump, and/or a patient-controlled analgesic (PCA) pump configured to deliver a medication (e.g., an anesthesia, such as propofol and/or remifentanil, and the like) to a patient. The pump 22 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like, or the pump 22 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like.

As shown in FIG. 6A, each of the pump 22, 24, 26, and 28 may be fluidly connected with an upstream fluid line 30, 32, 34, and 36, respectively. Moreover, each of the four pumps 22, 24, 26, and 28 may also fluidly connected with a downstream fluid line 31, 33, 35, and 37, respectively. The fluid lines can be any type of fluid conduit, such as tubing, through which fluid can flow. At least a portion of one or more of the fluid lines may be constructed with a multi-layered configuration as described herein.

Fluid supplies 38, 40, 42, and 44, which may take various forms but in this case are shown as bottles, are inverted and suspended above the pumps. Fluid supplies may also take the form of bags, syringes, or other types of containers. Both the patient care system 20 and the fluid supplies 38, 40, 42, and 44 may be mounted to a roller stand or intravenous (IV) pole 46.

A separate pump 22, 24, 26, and 28 may be used to infuse each of the fluids of the fluid supplies into the patient. The pumps 22, 24, 26, and 28 may be flow control devices that will act on the respective fluid line to move the fluid from the fluid supply through the fluid line to the patient 48. Because individual pumps are used, each can be individually set to the pumping or operating parameters used for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 6A. Many have check valves, drip chambers, valved ports, connectors, and other devices well known to those skilled in the art. These other devices have not been included in the drawings so as to preserve clarity of illustration. In addition, it should be noted that the drawing of FIG. 6A is not to scale and that distances have been compressed for the purpose of clarity. In an actual setting, the distance between the bottles 38, 40, 42, and 44 and the pump modules 22, 24, 26, and 28 could be much greater.

Referring now to FIG. 6B, an enlarged view of the front of the patient care system 20 is shown. The pump 22 may include a front door 50 and a handle 52 that operates to lock the door in a closed position for operation and to unlock and open the door for access to the internal pumping and sensing mechanisms and to load administration sets for the pump. When the door is open, the tube can be connected with the pump, as will be shown in FIG. 6C. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). The display 54 may otherwise be a part of or be coupled to the pump 22. Control keys 56 exist for programming and controlling operations of the pump as desired. The pump 22 also includes audio alarm equipment in the form of a speaker (not shown).

In the embodiment shown, a programming module 60 is attached to the left side of the pump 22. In some embodiments, the programming module 60 forms a part of the pump 22. Other devices or modules, including another pump, may be attached to the right side of the pump 22, as shown in FIG. 6A. In such a system, each attached pump represents a pump channel of the overall patient care system 20. In one embodiment, the programming module is used to provide an interface between the pump 22 and external devices as well as to provide most of the operator interface for the pump 22.

The programming module 60 includes a display 62 for visually communicating various information, such as the operating parameters of the pump 22 and alert indications and alarm messages. The programming module 60 may additionally and/or alternatively display the one or more patient parameters and the corresponding values for each of the one or more patient parameters described herein to the display 54 and/or the display 64. The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump. In some embodiments, the pump 22 may provide the entered values of each of the one or more patient parameters to the adjustment engine 110, which, in turn may determine or adjust a default value of a subsequent patient parameter based on one or more of the previously entered values of the one or more patient parameters. In some embodiments, the programming module 60 may communicate with the adjustment engine 110, include the adjustment engine 110, or implement features of the adjustment engine 110 described herein.

The communications system may take the form of a radio frequency ("RF") (radio frequency) system, an optical system such as infrared, a Blue Tooth system, or other wired or wireless system. The bar code scanner and communications system may alternatively be included integrally with the pump 22, such as in cases where a programming module is not used, or in addition to one with the programming module. Further, information input devices need not be hard-wired to medical instruments, information may be transferred through a wireless connection as well.

FIG. 6B includes a second pump 26 connected to the programming module 60. As shown in FIG. 6A, more pump modules may be connected. Additionally, other types of modules may be connected to the pump modules or to the programming module. In such implementations, the adjustment engine 110 may maintain determine, adjust, and/or display values (e.g., default values) of each of the one or more patient parameters for each pump (e.g., pump 22 and pump 26).

Turning now to FIG. 6C, the pump 22 is shown in perspective view with the front door 50 open, showing the upstream fluid line 30 and downstream fluid line 31 in operative engagement with the pump 22. The pump 22 directly acts on a tube 66 (also referred to as a pump segment) that connects the upstream fluid line 30 to the downstream fluid line 31 to form a continuous fluid conduit, extending from the respective fluid supply 38 (FIG. 6A) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 22, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 6C further shows a downstream pressure sensor 82 included in the pump 22 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 6A) and the flow control device, so that the connection of the correct fluid supply with the correct pump may be verified before any fluid is pumped to the patient.

With reference still to FIG. 6C, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 6A) and the flow control device, so that the connection of the correct fluid supply with the correct pump may be verified before any fluid is pumped to the patient. In an implementation where the source is a syringe, the flow control device 70 may be configured to press a plunger of the syringe to provide the infusion according to the programmed parameters.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

The term automatic, as used herein, may include performance by a computer or machine without user intervention; for example, by instructions responsive to a predicate action by the computer or machine or other initiation mechanism.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:

a display of an infusion device configured to deliver an analgesic substance to a patient, the display further configured to present at least one patient parameter of one or more patient parameters, wherein the infusion device includes a fluid channel to receive a tube and a pump configured to deliver the analgesic substance to the patient via the tube coupled to a fluid supply and received by the fluid channel;

a data storage in communication with the display, wherein the data storage comprises at least one data table comprising one or more default values corresponding to each value or range of values entered for each patient parameter of the one or more patient parameters, the one or more default values comprising a plurality of predetermined default values for a second patient parameter, each of the plurality of predetermined default values corresponding to a respective value or range of values of a first patient parameter, the plurality of predetermined default values being stored in the at least one data table prior to receiving a first entry;

at least one data processor; and at least one memory storing instructions which, when executed by the at least one data processor, result in operations comprising:

receiving, via a user interface of the display, the first entry, the first entry including a first value for the first patient parameter among the at least one patient parameter;

retrieving, based on the first entry, a default value for the second patient parameter from among the at least one patient parameter, from the data storage based on the received first parameter, wherein the retrieving comprises matching the first value of the first patient parameter to the respective range of values of the first patient parameter in the at least one data table and selecting a corresponding one of the plurality of predetermined default values for the second patient parameter;

presenting, on the display of the infusion device, the retrieved default value of the second patient parameter;

presenting, on the display of the infusion device, one or more adjustments to the retrieved default value of the second patient parameter, the one or more adjustments comprising one or more generated graphical elements configured to increment or decrement the retrieved default value of the second patient parameter;

determining a value for the second patient parameter based on the retrieved default value of the second patient parameter and a selection by a user via the user interface of at least one of the one or more adjustments;

determining, based on at least the value for the second patient parameter, a dose of the analgesic substance to be delivered to the patient; and causing, based on at least the determined dose, delivery of the analgesic substance to the patient via the tube and from the fluid supply.

2. The system of claim 1, wherein the operations further comprise:

receiving, via the user interface, a second entry, the second entry including a second value of the second patient parameter, the second value being an adjustment of the default value of the second patient parameter that is an accurate representation of the second patient parameter.

3. The system of claim 1, wherein the operations further comprise:

receiving, via the user interface, a confirmation for the presented retrieved default value of the second patient parameter.

4. The system of claim 1, wherein the operations further comprise:

presenting, on the user interface of the display, at least one of the at least one patient parameter.

5. The system of claim 1, wherein the infusion device comprises at least one of a target controlled infusion pump, a syringe pump, an anesthesia delivery pump, or a patient-controlled analgesic pump.

6. The system of claim 1, wherein the analgesic substance comprises at least one of a fluid, or a medication.

7. The system of claim 1, wherein at least one patient parameter comprises a value corresponding to at least one of a patient age, patient height, patient weight, patient gender, patient laboratory results, patient body mass index (BMI), or patient opiate usage.

8. The system of claim 1, wherein the first patient parameter and the second patient parameter are displayed simultaneously.

9. The system of claim 1, wherein the first patient parameter and the second patient parameter are displayed sequentially.

10. A computer-implemented method, comprising:

receiving, via a user interface of a display of an infusion device configured to deliver an analgesic substance to a patient, a first entry, the first entry including a first value for a first patient parameter among at least one patient parameter of one or more patient parameters, wherein the infusion device includes a fluid channel to receive a tube and a pump configured to deliver the analgesic substance to the patient via the tube coupled to a fluid supply and received by the fluid channel;

retrieving, based on the first entry, a default value for a second patient parameter from among the at least one patient parameter from a data storage, wherein the data storage is in communication with the display and comprises at least one data table comprising one or more default values corresponding to each value or range of values entered for each patient parameter of the one or more patient parameters, the one or more default values comprising a plurality of predetermined default values for the second patient parameter, each of the plurality of predetermined default values corresponding to a respective value or range of values of the first patient parameter, the plurality of predetermined default values being stored in the at least one data table prior to receiving the first entry, wherein the retrieving comprises matching the first value of the first patient parameter to the respective range of values of the first patient parameter in the at least one data table and selecting a corresponding one of the plurality of predetermined default values for the second patient parameter;

presenting, on the display of the infusion device, the retrieved default value of the second patient parameter;

presenting, on the display of the infusion device, one or more adjustments to the retrieved default value of the second patient parameter, the one or more adjustments comprising one or more generated graphical elements configured to increment or decrement the retrieved default value of the second patient parameter;

determining a value for the second patient parameter based on the retrieved default value of the second patient parameter and a selection by a user via the user interface of at least one of the one or more adjustments;

determining, based on at least the value for the second patient parameter, a dose of the analgesic substance to be delivered to the patient; and causing, based on at least the determined dose, delivery of the analgesic substance to the patient via the tube and from the fluid supply.

11. The method of claim 10 further comprising:

receiving, via the user interface, a second entry, the second entry including a second value of the second patient parameter, the second value being an adjustment of the default value of the second patient parameter that is an accurate representation of the second patient parameter.

12. The method of claim 10 further comprising:

receiving, via the user interface, a confirmation for the displayed retrieved default value of the second patient parameter.

13. The method of claim 10 further comprising:
presenting, on the user interface of the display, at least one of the at least one patient parameter.

14. The method of claim 10, wherein the infusion device comprises at least one of a target controlled infusion pump, a syringe pump, an anesthesia delivery pump, or a patient-controlled analgesic pump, and the analgesic substance comprises at least one of a fluid, or a medication.

15. The method of claim 10, wherein at least one patient parameter comprises a value corresponding to at least one of a patient age, patient height, patient weight, patient gender, patient laboratory results, patient body mass index (BMI), or patient opiate usage.

16. The method of claim 10, wherein the first patient parameter and the second patient parameter are displayed simultaneously or sequentially.

* * * * *